United States Patent [19]

Grell et al.

[11] 4,187,559
[45] Feb. 12, 1980

[54] BODY JOINT ENDOPROSTHESIS

[75] Inventors: Helmut Grell, Aalen; Achim Engelhardt, Frankfurt, both of Fed. Rep. of Germany

[73] Assignee: Sybron Corporation, Rochester, N.Y.

[21] Appl. No.: 914,738

[22] Filed: Jun. 12, 1978

Related U.S. Application Data

[63] Continuation of Ser. No. 672,963, Apr. 2, 1976, abandoned.

[30] Foreign Application Priority Data

Apr. 4, 1975 [DE] Fed. Rep. of Germany ...... 2514793

[51] Int. Cl.² .............................................. A61F 1/24
[52] U.S. Cl. ...................................... 3/1.91; 3/1.912; 3/1.913; 128/92 C; 128/92 EB; 128/92 EC
[58] Field of Search ........................... 3/1.9–1.913; 128/92 C, 92 CA

[56] References Cited

U.S. PATENT DOCUMENTS

| | | |
|---|---|---|
| 3,656,186 | 4/1972 | Dee ............................. 3/1.91 |
| 3,696,446 | 10/1972 | Bousquet et al. ........... 3/1.911 |
| 3,708,805 | 1/1973 | Scales et al. ................ 3/1.91 |
| 3,848,276 | 11/1974 | Martinez .................... 3/1.911 |
| 3,909,854 | 10/1975 | Martinez .................... 3/1.911 |
| 3,924,275 | 12/1975 | Heimke et al. ............. 3/1.912 |
| 4,051,559 | 10/1977 | Pifferi ........................ 3/1.912 |

FOREIGN PATENT DOCUMENTS

| | | |
|---|---|---|
| 2154338 | 5/1973 | Fed. Rep. of Germany ........... 3/1.911 |
| 2340546 | 2/1975 | Fed. Rep. of Germany ........... 3/1.91 |

*Primary Examiner*—Ronald L. Frinks
*Attorney, Agent, or Firm*—Theodore B. Roessel; James A. Rich

[57] ABSTRACT

A body joint endoprosthesis includes an anchoring member having a shaft anchored in a first bone and a pivot member connected to the anchoring member by a pivot joint. The pivot member includes a first body joint member and a support element that bears against a seating surface of the first bone. The first body joint member and a second body joint member, connected to the second bone, form the body implant joint.

32 Claims, 34 Drawing Figures

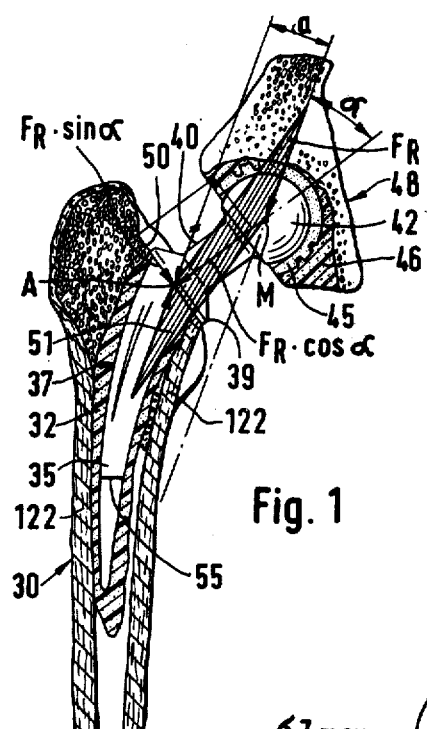
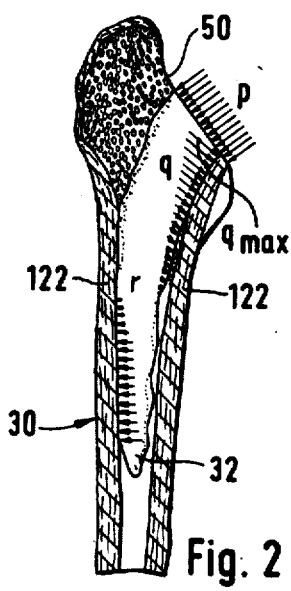
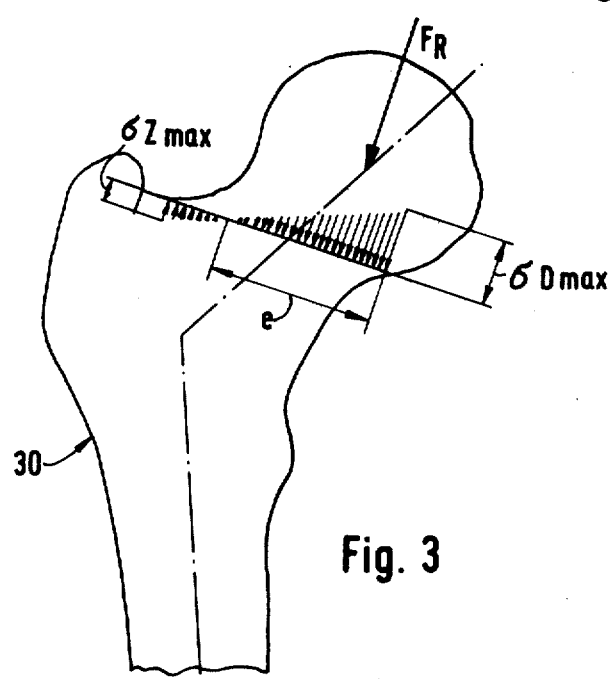
Fig. 1
Fig. 2
Fig. 3

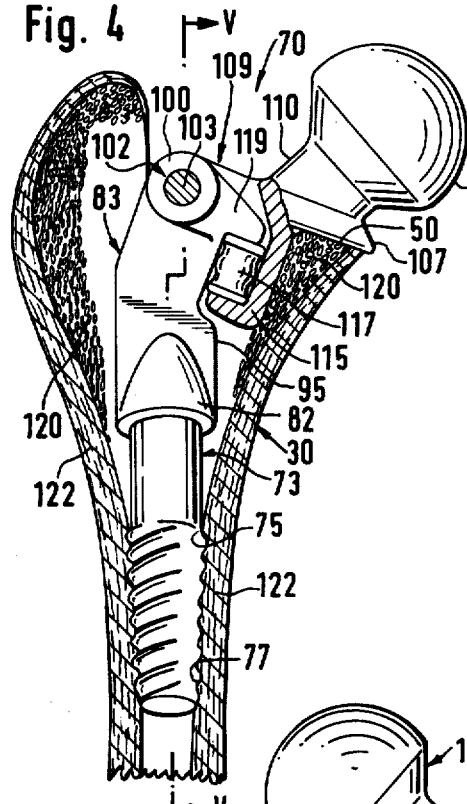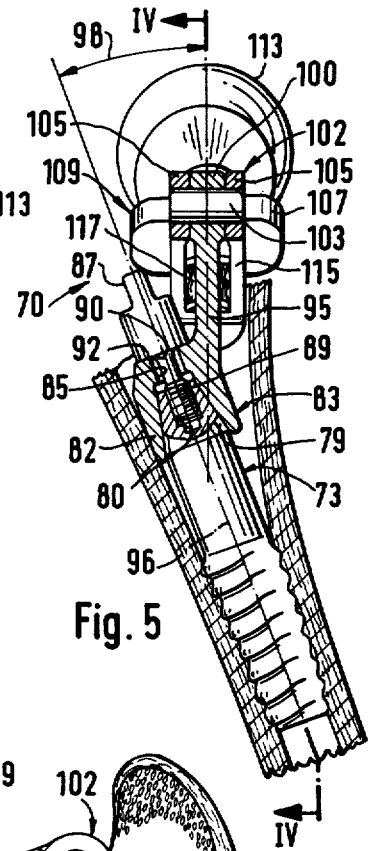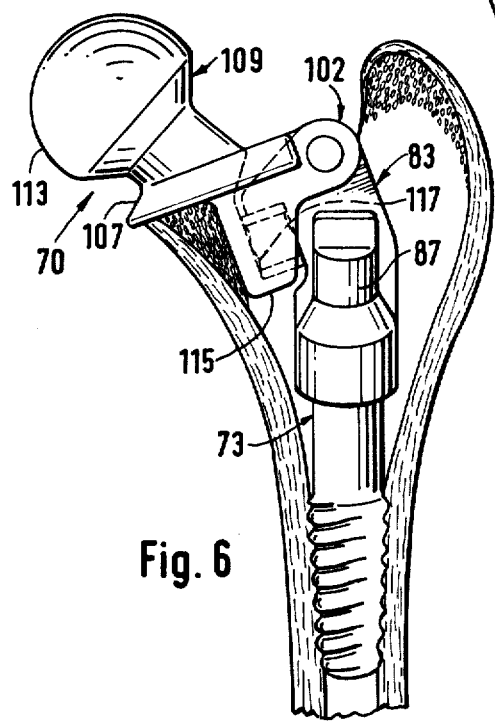

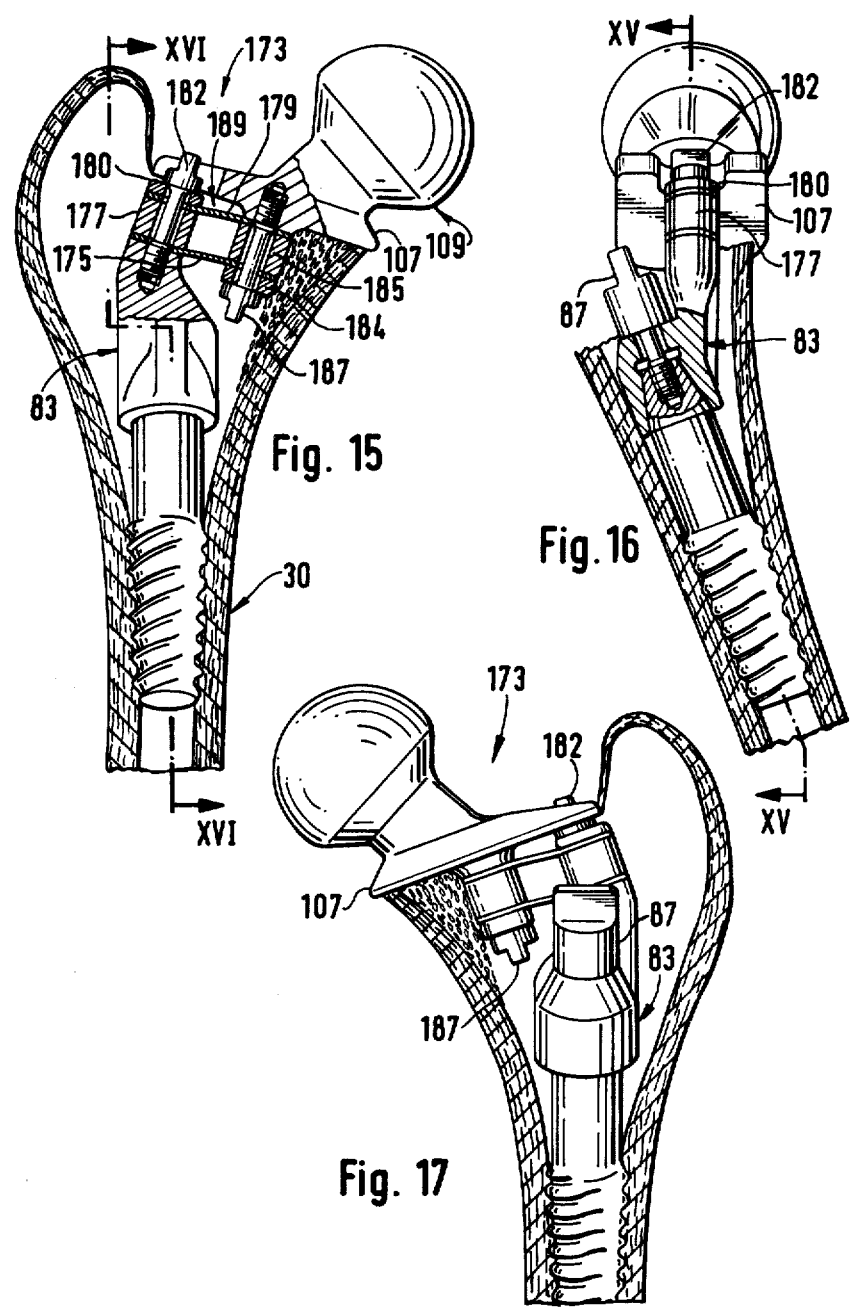

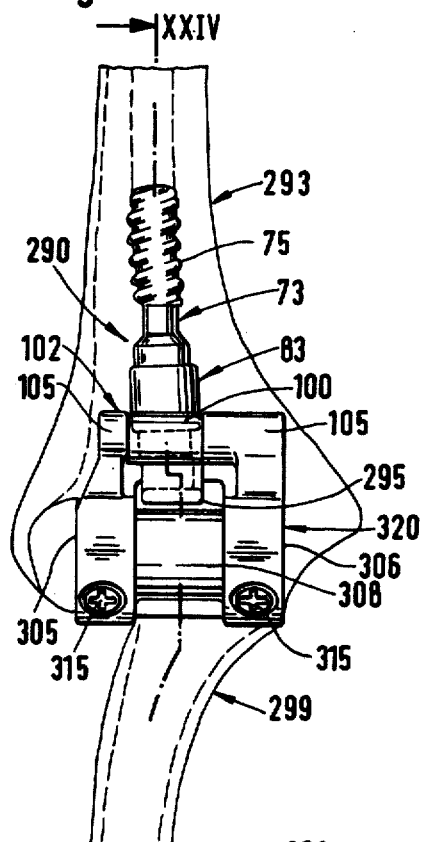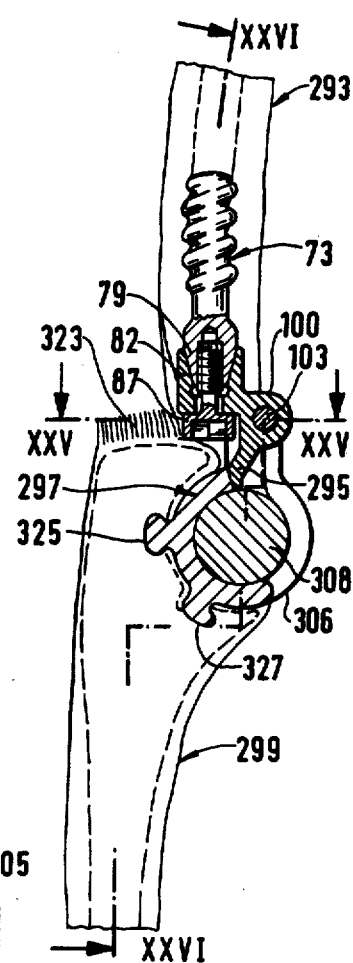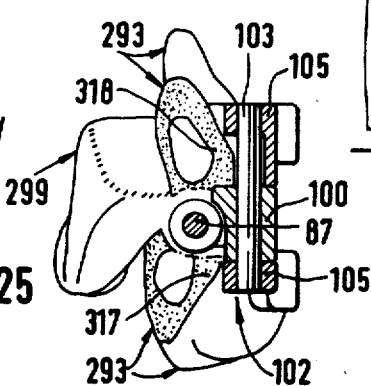

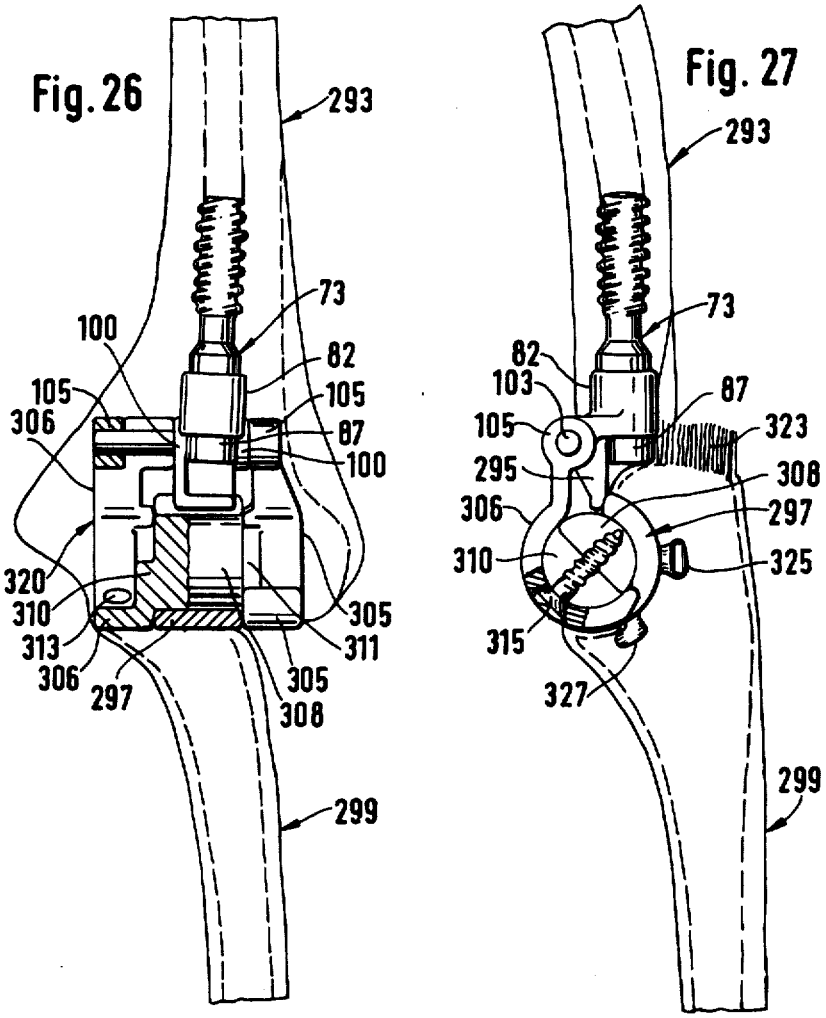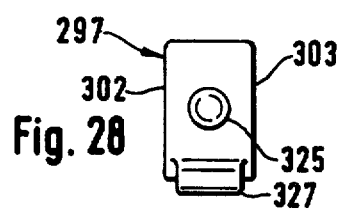

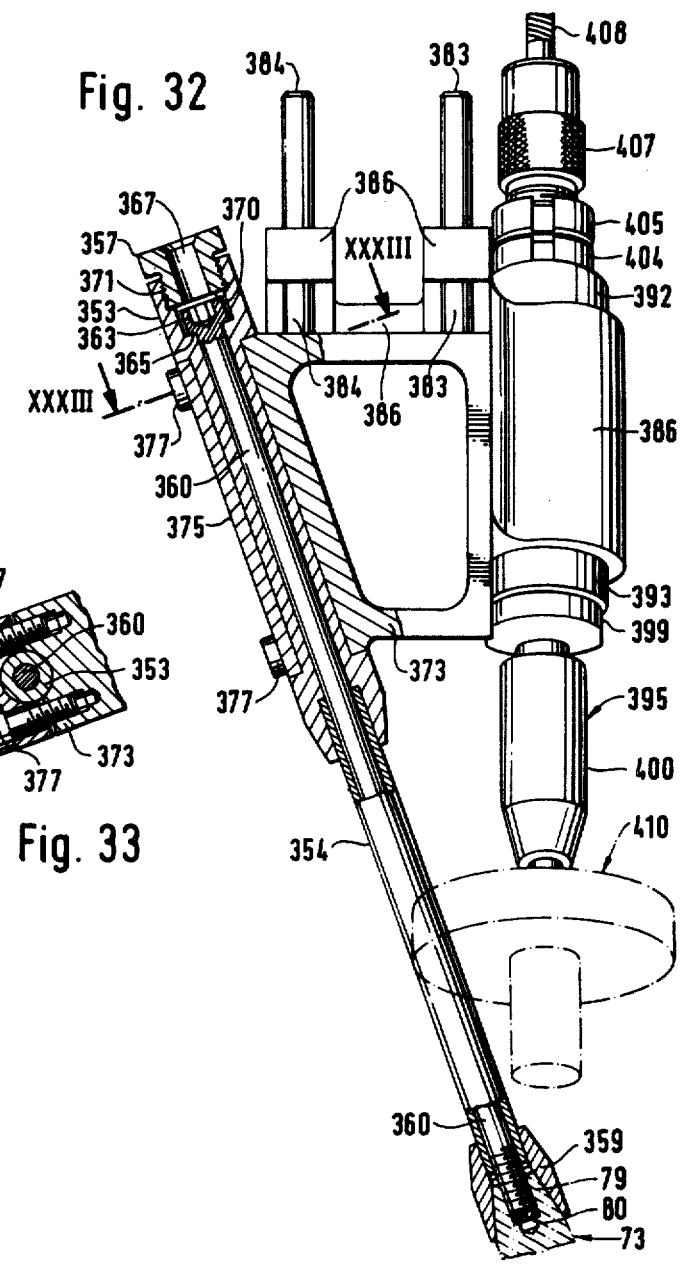

BODY JOINT ENDOPROSTHESIS

This is a continuation of application Ser. No. 672,963, filed Apr. 2, 1976 now abandoned.

BACKGROUND OF THE INVENTION

This invention relates to a body joint endoprosthesis, and more particularly to an endoprosthesis that transmits forces in a manner more closely approximating normal physiological stress distribution.

Wear phenomena in the joints of aged people, the consequence of inherited disease, rheumatic inflammatory ailments and injuries may lead to chronic pain conditions and progressive restriction of joint mobility (arthrosis), which often severly limits the sphere of activity and imposes acute physical stress upon the sufferer.

By way of showing the state of the art, reference is made to the paper "Technischer Fortschritt bei kunstlichen Huftgelenken" in the periodical *Technische Rundschau Sulzer*, 4/1974, pages 235 to 245. This treatise gives a review of the development of artificial hip joints and describes typical constructional forms known since 1939. From the discussion in the paper of these particular structural forms, it is apparent that all of the constructions have more or less serious inherent disadvantages. In addition to wear phenomena in the two parts of the joint, the ball and the socket, the known shaft prosthesis are accompanied by the particular disadvantage that loosening of the sockets and the shafts occurs, accompanied in certain cases by the subsequent breakage of the shaft. In the known artificial hip joints, this loosening of the shaft can be attributed to several different causes. Firstly, the shaft is preferably cemented into the bone. The cement which is used is the self-polymerizing synthetic plastic material methyl methacrylate. The heat of polymerization resulting from the curing of this material results in temperatures of 80° to 100° C. and can cause thermal damage of the surrounding tissue, because the coagulation point of albumen amounts to 56° C. In addition to these thermonecroses, damaging effects are also revived which resulted from the mechanical preparation of the bone (rasping or similar operations) carried out during the preparation of the seating to receive the implant, and at the same time there is formed between the damaged area and the bone a screen of connective tissue, which has a negative influence upon the anchorage in the bone. The screen of connective tissue permits micro relative displacements to take place between the implant and the bone seating. For a fuller treatment of this condition, reference is made to the book *Biopolymere und Biomechanik von Bindegewebssystemen*, Springer-Verlag 1974, pages 417 to 419, in the article "Zur Problematik der Zementverankerung im Knochen" by H. G. Willert.

A further cause of the loosening phenomenon is the nonphysiological nature of the application of force from the implant to the bone. For the want of any other exposition on this subject in the known art, an explanation thereof will now be given with reference to FIGS. 1, 2, and 3 of the accompanying drawings.

In FIG. 1 a shaft 35 of a femur head endoprosthesis 37 is secured in a thigh bone 30 by means of cement 32. The shaft 35 has a collar 39 and a neck 40 extension terminating in a ball 42 having a center point M. The ball 42 rests in a ball socket 45, which is secured in a pelvic bone 48 by cement 46. The resulting force $F_R$ passes through the center point M of the ball 42 and in FIG. 1 is shown in the direction in which this resultant force has its maximum value. In that case, the direction of the force with respect to the longitudinal axis of the neck 40 encloses an angle $\alpha$. If this resultant force $F_R$ is reduced to a point A of the seating surface 50 of the thigh bone 30 cooperating with the collar 39, then there will act in a direction normal to the seating surface 50 the force $F_R \cdot \cos \alpha$ and in the direction of the seating surface 50 the force component $F_R \cdot \sin \alpha$. In addition, due to the parallel displacement of the resultant force $F_R$ there is also effective the force couple $F_R \cdot a$ in accordance with the parallelogram surface 51 shown hatched in FIG. 1. The distance a represents the shortest spacing of the point A from the line of action of the resultant force $F_R$.

In FIG. 2 there are indicated qualitatively the surface pressures acting upon the thigh bone 30 and resulting from these two force components and the force couple. It is seen that the surface pressure p acting normal to the seating surface 50 is practically constant, while in the physiological case, represented in FIG. 3, the approximately linear curve of the normal stress $\sigma$ acting at the right hand or medial edge in FIG. 3 shows a maximum compression stress of $\sigma_{D\ max}$. In the physiological case according to FIG. 3 there will be a neutral fiber at a position spaced by a distance e from this position of maximum compression stress so that remote from it at the left hand or lateral edge in FIG. 3 there will be a tensile stress $\sigma_{Z\ max}$.

In the physiological case according to FIG. 3 practically no normal stress arises at right angles to the direction of the fibres of the cortical tissue 122 indicated in FIGS. 1 and 2, but in the other case the force component $F_R \cdot \sin \alpha$ and the force couple $F_R \cdot a$ will give rise to the surface pressures q and r, which act at right angles to the inner surface of the cortical tissue. The surface load q at the inner medial margin of the seating surface 50 has a maximum $q_{max}$, which, in the course of the continuous reconstitution of the bone, results in a progressive yielding of the bone.

Along with this yielding of the bone, the bending stress of the prosthesis and the cement increases until, due to further loosening of the shaft 35, cracks appear in the cement cladding 32, and finally a breakage 55 of the shaft 35 causes the prosthesis to fail and leads to immobility of the patient. The relative movements between the collar 39 and the seating surface 50 arising from this loosening process prevent the desirable progressive ingrowth of the bone cells into pores, cavities or perforations in the surface of the known prostheses. The above mentioned cracks in the cement cladding lead to intense corrosion phenomena in the metal (crack corrosion). Sinking of the shaft prosthesis is also possible if the support afforded by the cortical tissue is lost.

The force $F_R \cdot \cos \alpha$ indicated in FIG. 1 as acting at right angles to the seating surface 50 is transmitted through the collar 39, and, in respect of one part, over the seating surface 50 into the thigh bone 30 and, in respect of another part, is transmitted onto this thigh bone by virtue of the positive connection between the implant and the thigh bone 30. If it is assumed that the case under consideration is a known implant of steel, then the relationship of the modulus of elasticity of the steel implant to that of bone is about 8:1. Consequently, under load the bone deformation is relatively greater than that of the steel, and there is a relative displacement of the contacting surfaces of the implant and the bone. These displacements can lead to shearing off of the osteoblasts building up to form a bridge between the bone and the implant, which otherwise are desirable for a lasting anchorage of the implant in the bone. As a result, there is formed in that region a resilient screen of connection tissue, which permits further relative displacements and therefore a loosening of the prosthesis.

In the book entitled *Gesammelte Abhandlungen zur funktionellen Anatomie des Bewegungsapparates* by Friedrich Pauwels, Springer-Verlag 1965, in particular at pages 4 to 6 of the chapter "Mechanische Faktoren bei der Frakturheilung," a general description is given of the influence of mechanical stimuli upon the final structure of newly formed tissue in the form of connective tissue, cartilage or bone. The force component $F_R \cdot \sin \alpha$ defined above in connection with FIG. 1 can result in the setting up of a so-called free shearing force in the seating surface, preventing the desirable growth of new bone tissue, this force being explained in the above cited book of Pauwels in the chapter "Die freie Scherkraft" at pages 21 to 24.

Furthermore, attempts are also known to anchor shaft prosthesis in thigh bone without the use of cement. For this purpose the surface of the shaft is provided with perforations or macroscopic depressions, in which it is intended that there shall be a newly formed growth of bone tissue resulting in an intimately contacting anchorage of the shaft of the prosthesis in the thigh bone. Nevertheless, because the implantation of hip joint endoprostheses is mostly necessary in elderly patients, great importance must be placed upon early mobilization of the patient. If the patient is laid up for too long a time until there is a sufficiently firm ingrowth of the shaft of the prosthesis, this delay can, for example, cause the risk of pneumonia, muscular atrophy and damage to the heart and circulation as well as to the bladder and kidney system. For example, in experiments with animals, the time taken for the formation of load bearing bone tissue has been at least two months. Consequently, the known types of prostheses whose anchorage in the thigh bone relies exclusively upon the principle of the ingrowth of bone tissue are therefore very disadvantageous on account of the lack of early mobilization of the patient. Moreover, because of the difference in the moduli of elasticity and locally high surface pressures, loosening phenomena can appear at the implant.

In known hip joint endoprostheses of this type (German Auslegeschrift Specification No. 1,541,246, and French specification No. 2,057,418) a metallic shaft is formed integrally with a collar shaped support element and a bearing stud, upon which a ball head is rotatably mounted as the first part of the joint. There is no joint between the support element and the shaft. In consequence this construction does not remove the above explained disadvantages.

In a further known hip joint endoprosthesis of the above mentioned type (French specification No. 2,210,909) a shaft is formed integrally with a collar shaped support element, to which can be screwed a first joint member in the form of a ball head to form a rigid unit secured by a clamping device. This construction also lacks a joint between the support element and the shaft.

In the Swiss patent specification No. 426,096 there is disclosed a hip joint endoprosthesis, to whose shaft there is integrally connected a first socket. In this socket there is mounted a freely rotatable ball forming the first joint member, which latter is also supported in a socket in the pelvis bone forming the second joint member. There is thus the lack of a support element and accordingly also a lack of the joint according to the present invention. The forces applied to the first socket are transmitted exclusively through the shaft into the thigh bone, so that the abovementioned disadvantages are even more clearly noticeable.

It is already known (German Offenlegungsschrift Specification No. 2,432,766) to construct an artificial knee joint which during the whole of the movement cycle functions as a crossed quadrangular linkage having the bridge connected to the thigh bone and the couple connected to the tibia.

SUMMARY OF THE INVENTION

An object of the present invention is to provide a body joint endoprosthesis wherein the transmission of force into a first bone takes place analogously to the physiological condition in such a manner that the stress distribution in the first bone corresponds, at least to a good approximation, to the physiological stress distribution. For the purpose of promoting the growth of new bone in the seating surface, relative movements between the seating surface and the support element should as far as possible be avoided. The anchorage in the first bone should take place without the use of cement. It should be possible to provide for the early mobilization of the patient.

The invention provides a body joint endoprostheses including an anchoring part having a shaft adapted to be anchored in a first bone, and a pivot member connected to the anchoring part by a pivot joint. The pivot member includes a first body joint member and a support element adapted to bear against a seating surface of the first bone. The first joint member, and a second joint member adapted to be connected to a second bone, form the body implant joint. The transmission of force from the supporting element into the seating surface is analogous to the physiological condition, while affording the stressing conditions which are necessary for the maintenance of the bone tissue. The ingrowth of bone tissue into the openings and pores of the prosthesis is considerably facilitated and the time taken for this process is shortened. The joint resolves disadvantageous stiffness of the prosthesis, and while maintaining the necessary functional stability affords mobility within the prosthesis itself, which removes the above described disadvantages.

According to one practical form of the invention, the pivot joint is in the form of a hinge joint. The resulting ability of the pivot member to pivot only in one plane is adequate in most cases to provide a transmission of force into the first bone approximating to a large extent to the physiological condition. However, if universal pivotability of the pivot member is desired with respect to the seating surface, the joint may be a ball joint or a Cardan joint.

The joint may also be a knife edge type of construction or an elastic joint. In the last mentioned case, the joint may include at least one resilient member, preferably a leaf spring, clamped between the anchoring part and the pivot member, with the resilient member or members being prestressed to force the supporting element onto the seating surface. The prestress may produce a surface pressure of, for example, 0.1 to 0.5 Newtons per square millimeter ($N/mm^2$) on the seating surface. This surface pressure reinforces the tension of the postoperative weakened muscles and, during the ingrowth period, prevents lifting of the pivot member from the bone section surface. Moreover, this surface pressure exerts an additional stimulus upon the bone structure of the spongiose tissue and the cortical tissue of the seating surface and favors the growth of bone into suitable reception openings or pores of the supporting element.

For the purpose of guiding the supporting element in parallel relation to the seating surface it is possible in accordance with the invention to arrange two resilient members in a pivot plane of the pivot member and spaced from each other in the manner of a parallelogram.

According to one practical form of the invention applied to a hip joint endoprosthesis, the first bone is a thigh bone, the first joint member is a ball and the support element is a collar rigidly secured to the ball. This produces a robust and simple construction. The axis of the joint may be situated at least approximately in a plane containing the seating surface. This produces a quasi-physiological transmission of force from the collar to the seating surface.

In this form of the invention the second bone is a pelvic bone and the second joint member is a ball socket anchored in the pelvic bone. The socket is preferably anchored in the bone by three studs arranged at the corners of a triangle so that the maximum resultant force upon the body joint passes at least approximately through the surface center of gravity of the triangle.

In another practical form of the invention, an elbow joint endoprosthesis, the first bone is an upper arm bone, the first joint member is a hinge pin, and the support element includes two condylar shells arranged in spaced relation to each other and connected to the ends of the hinge pin. In this case also there is afforded a quasi-physiological transmission of force from the condylar shells to the oppositely situated seating surface.

According to a further feature of the invention the shaft is provided with an external sawtooth thread, whose comparatively steep flanks are directed towards the pivot member. The comparatively steep flanks of the sawteeth allow a kind of barbed hook anchorage of the shaft to take place in the bone, and can be directed at least approximately normal to the longitudinal axis of the shaft. This asymmetrical shape of the sawtooth is significant because the force $F_Z \cdot \cos \beta$ acts always in one direction, which is in fact the upward direction, and thus substitutes the physiological tensile stresses. Upon the flanks of the thread directed normal to the longitudinal axis of the shaft there will be no radial force resulting from the force $F_Z \cdot \cos \beta$, which could exert upon the bone a non-physiological bursting effect.

Another object of this invention is to provide an instrument for the insertion and removal of body joint endoprostheses described above. According to the invention, a rotary tool is adapted to be rigidly connected to the shaft of the anchoring part. This facilitates screwing the shaft into or out of a tapped hole in a bone without producing any bending movements. Undesired stresses upon the bone are thus avoided.

A holder having a guide device for a milling tool is preferably adjustably secured to this rotary tool. By virtue of the stiffness of the rotary tool and its coupling to the shaft it is possible to perform the necessary milling operations upon the bone which is to receive the shaft, and to do this in perfectly determinate geometric relationship with reference to the shaft. During this operation, the shaft therefore operates as a reference body anchored in the bone which is to be milled in the same way as later, after the removal of the instrument, it will be used for the remaining operation of mounting the endoprosthesis upon the shaft. In this manner, precise cooperation of the respective prosthesis with the bone parts to be milled is ensured.

Other objects and advantages of this invention will be seen from the following detailed description.

DRAWINGS

FIG. 1 is a cross-sectional view illustrating the resolution of forces in prior art hip joint endoprostheses.

FIG. 2 is a sectional view illustrating how the prior art hip joint endoprosthesis illustrated in FIG. 1 transmits forces to the femur.

FIG. 3 is a schematic view illustrating stress distribution in the physiological femur.

FIG. 4 is a femur head endoprosthesis with a hinge joint in section along the line IV—IV of FIG. 5.

FIG. 5 is a side elevation in section along the line V—V of FIG. 4.

FIG. 6 is a side elevation from the left of the representation in FIG. 5 with the thigh bone in section.

FIG. 15 is essentially the sectional elevation along the line XV—XV of FIG. 16 showing another femur head endoprosthesis with an elastic joint.

FIG. 16 is the partial sectional elevation along the line XVI—XVI of FIG. 15.

FIG. 17 is the side elevation from the left of the view shown in FIG. 16 with a longitudinally sectioned thigh bone.

FIG. 23 is a front elevation of a right hand elbow joint endoprosthesis (without bearing shell).

FIG. 24 is a sectioned elevation along the line XXIV—XXIV of FIG. 23.

FIG. 25 is the sectioned elevation along the lines XXV—XXV of FIG. 24.

FIG. 26 is the sectioned elevation along the line XXVI—XXVI of FIG. 24.

FIG. 27 is the partially sectioned elevation from the right hand side of the view in FIG. 23.

FIG. 28 is a plan view of the bearing shell in FIGS. 24, 26 and 27.

FIG. 29 is a side elevation from the left hand side of the bearing shell according to FIG. 28.

FIG. 32 is a side elevation of the instrument with a longitudinally sectioned rotary tool.

FIG. 33 is the sectional elevation along the line XXXIII—XXXIII of FIG. 32.

DETAILED DESCRIPTION

Figure 7:
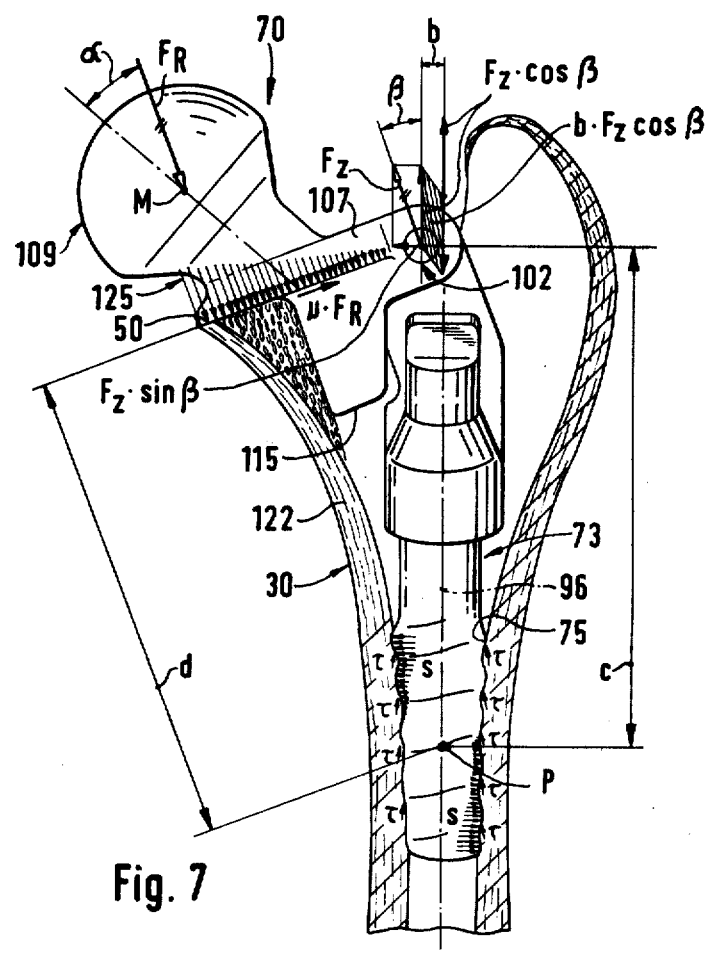
FIG. 7 is a schematic diagram corresponding to that of FIG. 6 with practical operating quantities inserted.

FIGS. 4, 5 and 6 illustrate a femur head endoprosthesis 70 embodying this invention. Preferably, at least the external surfaces of the endoprosthesis consist of metal coated with enamel, i.e., with a vitreous or partially devitrified inorganic coating bonded to the metal at a temperature above 800° F. The metal and enamel constitute a compound body, in which the components of the compound, i.e., the metal and the enamel, can be selected and adjusted both with respect to each other and with respect to the particular demands of the situation to give the optimum results. This compound material is ideally biocompatible and possess technical, physical and chemical characteristics which are superior to all known materials used for prostheses.

A shaft 73 coated with enamel and provided with an external rounded thread 75 is screwed into the internal thread 77 of the thigh bone 30. The external rounded thread 75 provides complete anchorage of the shaft in the bone without bone cement, mastic or the like while still achieving an exceptionally good degree of positive and/or non-positive connection between the shaft and the bone.

Preferably the thread 75 of the shaft is conically formed in a manner complementary to the oppositely situated internal wall of the thigh bone 30. The maximum degree of care of the bone and a reliable anchorage of the shaft therein are achieved if the internal thread 77 is cut in advance by means of a thread core boring and tapping drill or milling tool, not shown in the drawing, before the shaft is screwed into the bone.

The metallic shaft 73 is surmounted by a cone 79 which is also enamelled and ground to a finish and has a threaded bore 80, which is not enamelled. Upon the cone 79 there is releasably mounted an extension member 83 having a conical socket 82 complementary to the cone 79. A screw 87 penetrates with appropriate clearance a bore 85 in the conical socket 82 and has its non-enamelled thread 89 screwed into the tapped bore 80 for securing the conical socket 82 with respect to the cone 79. The underside 90 of the screw head and the opposing reception surface 92 of the conical socket 82 are enamelled and are ground to make a liquid tight connection. Screw 87 may be locked in place with liquid synthetic plastic adhesive.

This construction permits a continuous rotary adjustment and fixing of the conical socket 82 with respect to the cone 79 of the shaft. Even when a comparatively small axial compression force is exerted by the screw 87, the cone type of connection affords substantial load bearing frictional forces which insure a reliable functioning of the prosthesis. Even when the shaft 73 is completely enamelled, the cone type of connection permits satisfactory working of the shaft for the purpose of fitting and fluid tightness, for example by grinding. The tapped bore 80 and the threads 89 of the screw do not have to be enamelled, because it is possible by suitable working of the opposing enamelled surfaces to obtain a perfect seal between the screw head and the conical socket, which prevents the ingress of body liquids and secretions.

An arm 95 extends upwardly from the conical socket and, as may be seen in FIG. 5, encloses an angle 98 with the longitudinal axis 96 of the shaft 73. The upper end of the arm 95 carries a hinge eye 100 of a hinge joint 102. A hinge pin 103 penetrates both the hinge eye 100 and a fork 105, formed upon the collar 107 of a pivot member 109 that bears upon the seating surface 50 of the thigh bone 30. The collar 107 is rigidly connected through a neck 110 to a ball 113. From the underside of the collar 107 extends a bearing pocket 115 for a spring 117 of silicone rubber, which supports itself at the other side upon a support arm 119 of the arm 95.

The use of the extension member 83 releasably connected to the shaft 73 makes it possible to preassemble the pivot member 109, the joint 102 and the extension member 83 before this structural group is implanted. This shortens the operating time and also allows, for example, a complete enamelling of the surface to be effected. The complete structural group can also be subjected, before implantation, to any desired specialized finishing treatment and quality control.

With the exception of the spring 117, which is also biocompatible, the entire external surface of the pivot member 109, the hinge joint 102 and the extension member 83 is enamelled. Those enamelled surfaces of the femur head endoprosthesis 70 which are situated opposite to spongy bone (spongiose tissue) 120 or bone scale (cortical tissue) 122 can be suitably prepared by roughening, creation of artificial pores or the like so as to present an optimum condition for the inward growth of bone tissue, and thus to achieve a very desirable secondary anchorage of the prosthesis in the thigh bone 30. The ingrowth process is reinforced by the fact that the spring 117 urges the collar 107 against the seating surface 50 and maintains definite load conditions on seating surface 50 when the load on the hip joint is relieved. Preferably, the collar 107 is pressed against the seating surface 50 with a surface pressure of 0.1 to 0.5 N/mm$^2$.

The pivot joint 102 and the quasi-physiological transmission of force into the bone that it provides relieve the shaft 73 of a substantial load as compared with the conditions existing in known shafts. Thus there is achieved, not only primarily an adequate anchorage of the shaft in the bone, but also secondarily a further improvement in the anchorage by growth of the bone into the shaft, which favors an early mobilization of the patient.

In FIG. 7 the operating quantities are plotted schematically. Analogously to the physiological condition shown in FIG. 3, the resultant force $F_R$ is transmitted as a substantially triangular surface load 125 onto the seating surface 50. As already explained in the physiological case according to FIG. 3, a tensile stress is effective outwardly or to the left hand side of the neutral fiber. In a similar way there will result from the presence of the hinge joint 102 a resultant tensile force $F_Z$, which, taking into consideration the angle $\beta$, can be resolved into its mutually normally directed components $F_Z \cdot \cos \beta$ and $F_Z \cdot \sin \beta$. The component $F_Z \cdot \cos \beta$ acts as a tractive force upon the shaft 73 and is transmitted through the outer round threads 75 thereof into the cortical tissue 122 of the thigh bone 30. In that region there will arise the thrust stresses $\tau$ indicated in FIG. 7.

The axis of the hinge joint 102 is laterally removed by a distance b from the plane in which is situated the longitudinal axis 96 of the shaft 73. This results in a force couple $b \cdot F_Z \cdot \cos \beta$, which acts in the same sense as a moment composed of a frictional force $\mu \cdot F_R$ and a lever arm d, which corresponds to the perpendicular spacing distance from the seating surface 50 to a center point P of that portion of the shaft 73 which is provided with the externally rounded thread 75. In the opposite sense there will act a moment consisting of the force component $F_Z \cdot \sin \beta$ and a lever arm c, the latter corresponding to the normal spacing distance from the center point P to the line of action of the force component $F_Z \cdot \sin \beta$. The moment resulting from the above mentioned force couple and the above mentioned two moments gives rise to the surface pressure s at the cortical tissue 122. If, for structural considerations, the spacing distance b is made equal to zero, the above mentioned force couple $b \cdot F_Z \cdot \cos \beta$ vanishes. The surface pressure s results then from the resulting moment $$\Sigma M = F_Z \cdot \sin \beta \cdot c - \mu \cdot F_R \cdot d$$

The deformation of the thigh bone 30 resulting from the surface load 125 acting upon the seating surface 50 turns the pivot member 109 about the axis of the hinge joint 102 and can in this way, in any occurring shape condition of the thigh bone 30, transmit the force into the thigh bone 30 in a manner analogous to the physiological conditions. From the lower margin of the bearing pocket 115 to the upper termination of the externally rounded thread 75 of the shaft 73 there will exist no positive connection between the femur head endoprosthesis 70 and its bearing in the thigh bone 30. By this means relative micro movements of the contact surfaces of the prosthesis and the bone are decisively reduced.

Figures 8, 9, 10:
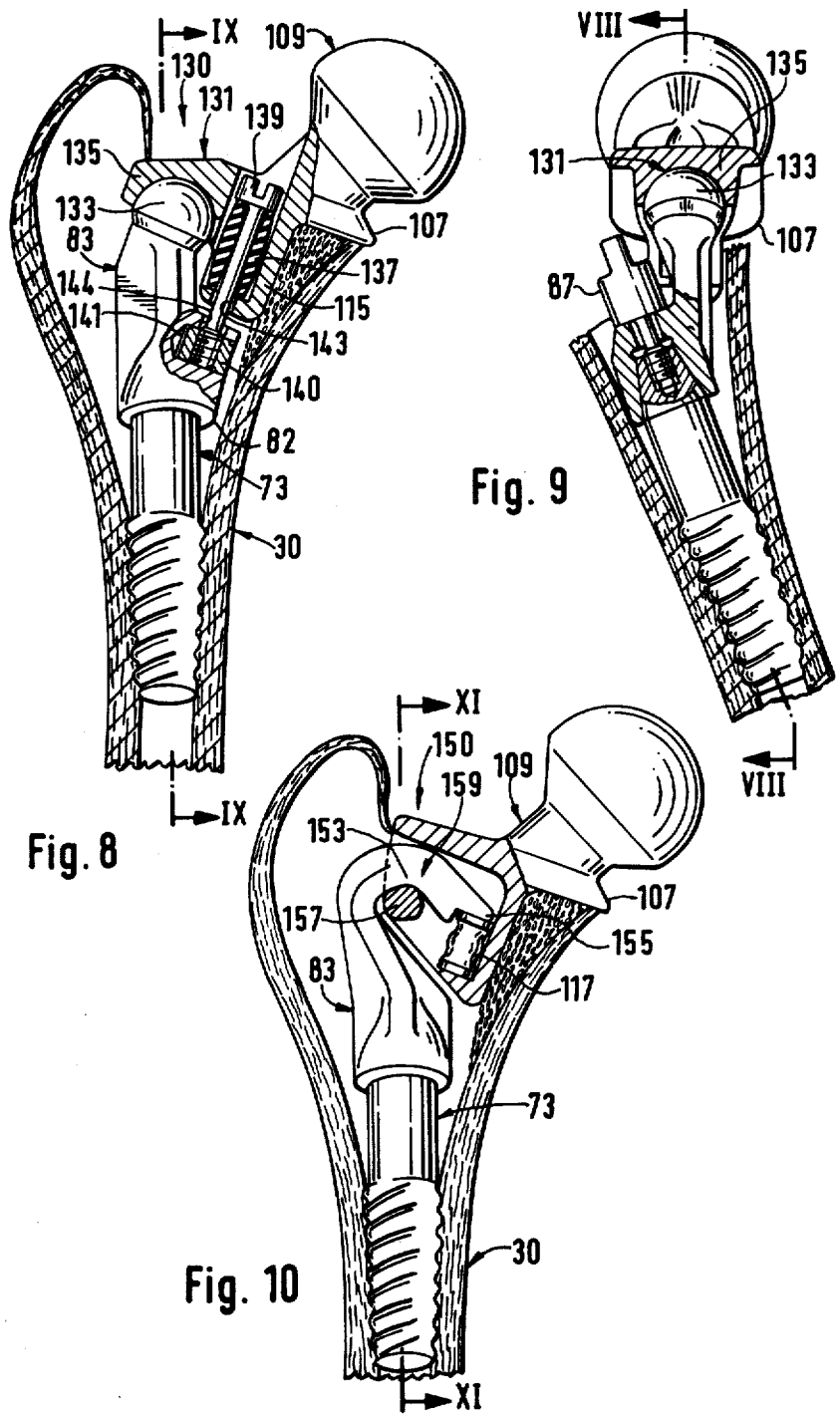
FIG. 8 is substantially a sectioned elevation along the line VIII—VIII of FIG. 9 of a femur head endoprosthesis with a ball joint.
FIG. 9 is the partially sectioned elevation according to line IX—IX in FIG. 8.
FIG. 10 is essentially a sectional elevation along the line X—X of FIG. 11 of a femur head endoprosthesis with a knife edge bearing construction.

FIGS. 8 and 9 show a femur head endoprosthesis 130, wherein the joint is designed as a ball joint 131. A ball 133 of the ball joint 131 is formed at the top of the extension member 83, while there is a ball socket 135 at the underside of the collar 107.

In the bearing pocket 115 is a spring 137, consisting, for example, of silicone rubber having a hardness of A 70±5 Shore, and having an axial aperature. Through this aperature leads a clamping screw 139, which is screwed into a pivot stud 140 mounted in a bore 141 in the extension member 83. The clamping screw 139 permits the surface pressure exerted by the collar 107 on the seating surface 50 to be finely adjusted. This screw may be locked in position by means of liquid synthetic plastic adhesive.

The screw 139 also leads through holes 143 and 144 in the bearing pocket 115 and the extension member 83, while allowing sufficient lateral clearance therein to provide for any swinging movement. Likewise adequate lateral clearance is provided for the head of the screw 139 so that the pivot member 109 can have motion universally about the ball joint 131 and can afford particularly uniform force transmission into the thigh bone 30.

Figures 11, 12, 13, 14:
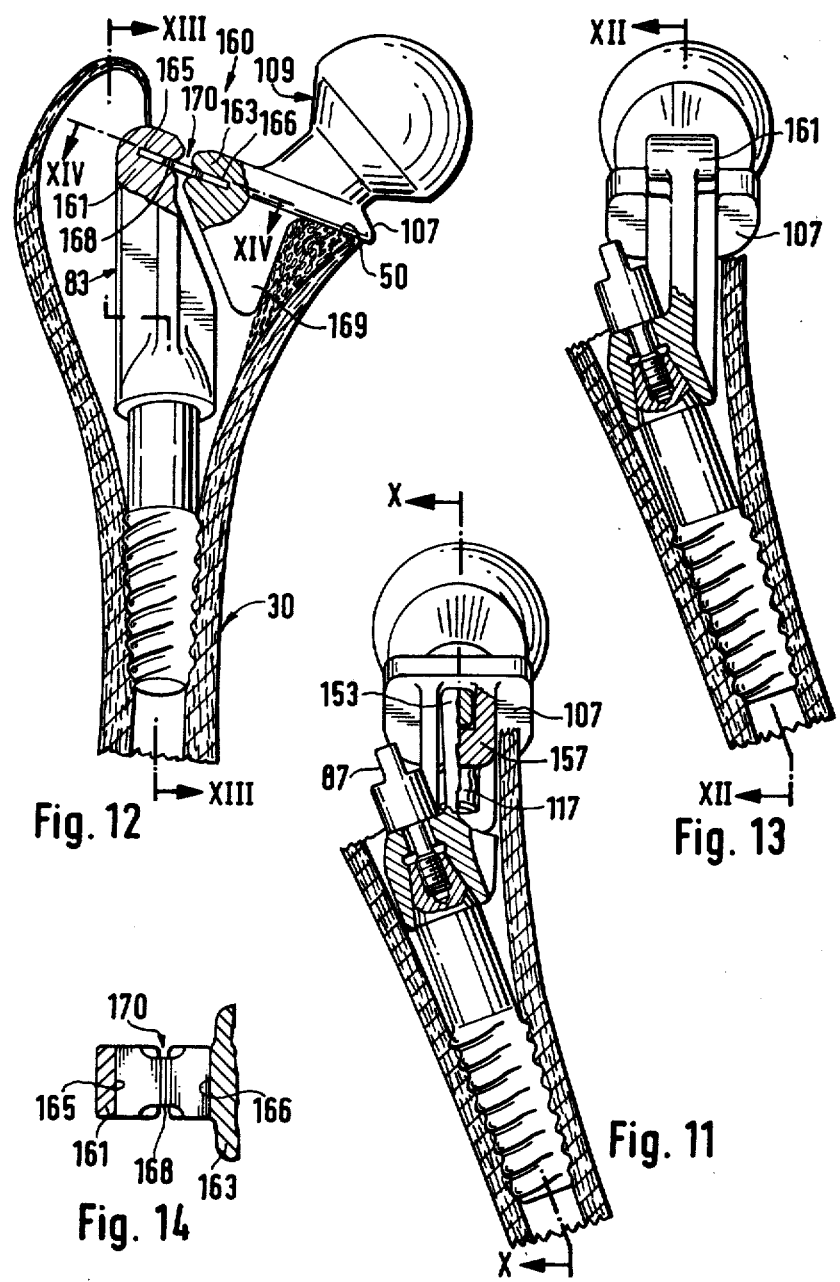
FIG. 11 is a partly sectioned elevation along the line XI—XI of FIG. 10.
FIG. 12 is essentially the sectional elevation along the line XII—XII of FIG. 13 of a femur head endoprosthesis with an elastic joint.
FIG. 13 is a partially sectioned elevation along the line XIII—XIII of FIG. 12.
FIG. 14 is the sectional elevation along the line XIV—XIV of FIG. 12.

FIGS. 10 and 11 show a further femur head endoprosthesis 150, wherein the extension member 83 has its head formed as a hook shaped knife edge bearing 153, whose free end 155 forms the upper abutment for the spring 117. At right angles to the knife edge 153 proceeds a counteracting knife edge 157, which is formed at the base of the collar 107. Moreover, the top of the knife edge 153 is in sliding engagement with the underside of the collar 107. The knife edge bearing 153 and the counteracting knife edge 157 form a knife edge bearing construction 159, which can be fully enamelled, as can also the ball joint 131 in FIGS. 8 and 9.

A further femur head endoprosthesis 160 is shown in FIGS. 12 and 13. They show a spring bearing 161 at the top of the extension member 83 and a further spring bearing 163 formed upon the collar 107. The spring bearing members 161 and 163 are each provided with a slot 165 and 166 respectively, in which a leaf spring 168 is secured, for example by adhesion or pressing in. Spring 168 is slightly prestressed in such a manner that the collar 107 is applied with the desired surface pressure to the seating surface 50 of the thigh bone 30. The edges of the slots 165 and 166 are strongly rounded off at the places where, otherwise, the deformation of the leaf spring 168 would result in undesirable edge pressures of large dimensions. In this construction, an extension 169 is formed at the base of the collar 107 for positive lateral guidance of the pivoting member with the bone as well as to increase the area of contact with respect to the surrounding bone tissue and thereby to enhance the conditions for ingrowth.

FIG. 14 shows the spring supports 161 and 163 and the leaf spring 168 inserted therein as viewed from a direction other than that shown in FIG. 12. The elastic joint is shown at 170.

FIGS. 15, 16 and 17 show a further femur head endoprosthesis 173, wherein there are mounted at the top of the extension member 83 in the following sequence a leaf spring 175, an intermediate ring 177, a further leaf spring 179 and a covering ring 180. The components 175 to 180 are penetrated by a clamping screw 182, which is screwed into the extension member 83 and axially compresses these components. The leaf springs 175 and 179 are thus effectively clamped upon the extension member 83. A similar clamping arrangement of the leaf springs 175 and 179 is provided upon the pivot member 109, where again the leaf springs 175 and 179 as well as a covering ring 184 and an intermediate ring 185 are penetrated and axially compressed by a clamping screw 187 which is screwed into the collar 107. The clamping screws 182 and 187 can be locked in their threaded position by means of liquid synthetic plastic material. This construction comprising the two leaf springs guided in parallelogram fashion also represents an elastic joint 189.

The leaf springs 175 and 179, like the leaf spring 168 in FIGS. 12 and 13, may consist of alloy spring steel, which may be coated, for example, with silicone rubber, to avoid the possibility of any metallic contact with parts of the body. All other parts of the femur head endoprosthesis 160 and 173 may again be fully enamelled.

Figure 18:
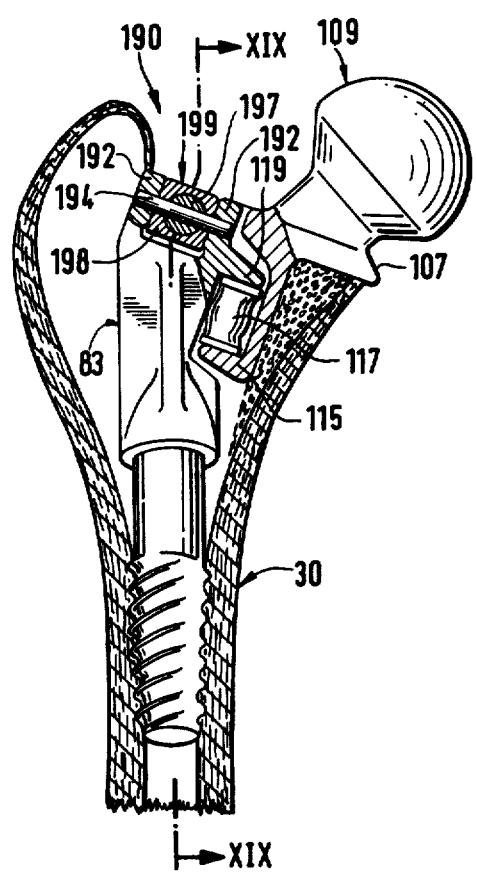
FIG. 18 is essentially the sectional elevation along the line XVIII—XVIII of FIG. 19 showing a femur head endoprosthesis with a Cardan joint.
Figure 19:
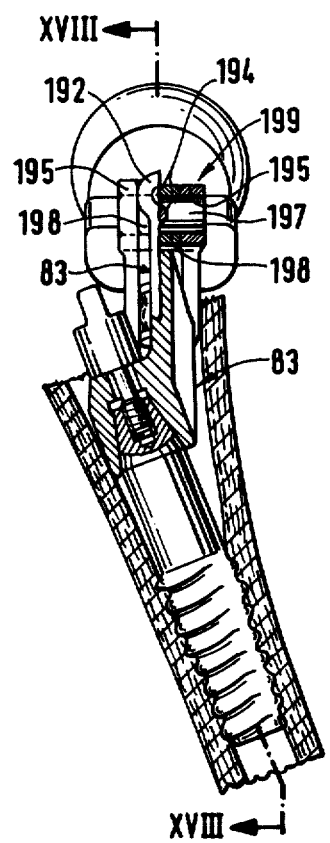
FIG. 19 is the partially sectioned elevation along the line XIX—XIX in FIG. 18.

FIGS. 18 and 19 show a femur head endoprosthesis 190, wherein at the upper end of the extension member 83 there is arranged a fork trunnion bearing 192 within which is rotatably mounted a hinge pin 194 passing through said fork. The pivot member 109 carries a further fork bearing 195, which is displaced through 90° with respect to the fork bearing 192 and is rotatably mounted upon a hinge pin 197, which is itelf penetrated at right angles by the hinge pin 194. Both of the hinge pins 194 and 197 penetrate a core 198 and form with the core the cross member of a Cardan joint 199, i.e., a universal joint consisting of a cross like piece, opposite ends of which rotate within the forked end of bearings 192 or 195. The Cardan joint 199, like the ball joint 131 of FIG. 8, permits a universal movement of the pivoting member 109 with respect to the thigh bone 30.

Figure 20:
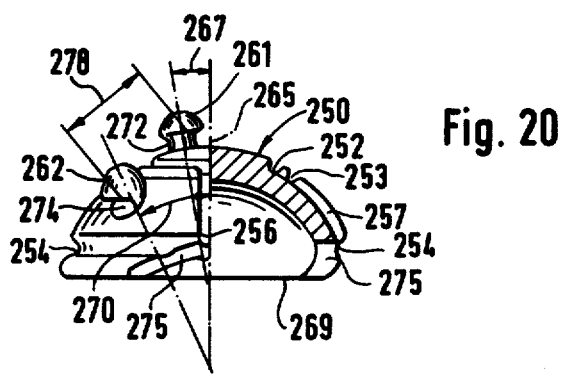
FIG. 20 is the partially sectioned elevation along the line XX—XX of FIG. 21 showing a ball socket.
Figure 21:
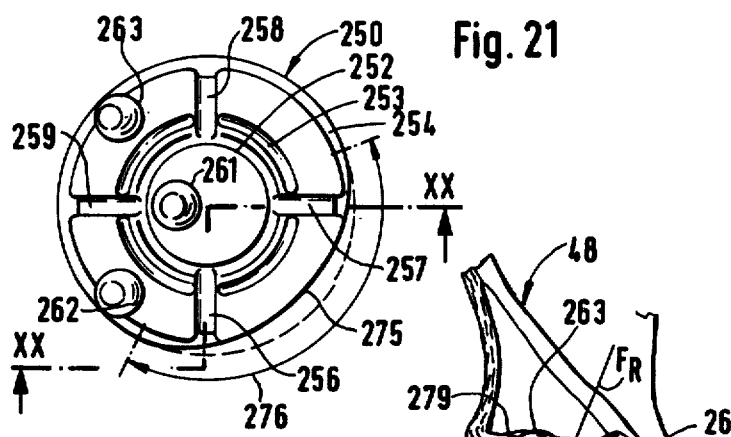
FIG. 21 is a plan view of the ball socket according to FIG. 20.

FIGS. 20 and 21 show a ball socket 250 for a total hip joint endoprosthesis. The external surface of the ball socket 250 is provided with concentric channels 252, 253 and 254 and with channels 256 to 259 located in planes extending through the axis 265 of the socket. These channels faciliate and promote the macroscopic ingrowth of new bone tissue into the surface of the ball socket and thereby effect secondary anchorage in the pelvic bone 48 (FIG. 22).

For the primary or temporary anchorage of the ball socket 250 in the pelvic bone 48 there are provided three studs 261, 262 and 263 of button shape, which are arranged at the corners of a triangle in such a manner that the maximum resultant force $F_R$ (FIG. 22) is directed at least approximately through the surface center of gravity or centroid of this triangle, i.e., at least approximately through the point where three lines, each of which extends from a corner of this triangle to the mid-point of the opposite side of the triangle, intersect. Stud 261 is positioned near the apex of the socket 250 and the other two studs 262 and 263 are positioned at approximately one-half the height of the socket. The easiest fitting and most secure anchorage of the ball socket is achieved if the axis of the three studs 261, 262 and 263 are positioned with their longitudinal axes in planes which are at least approximately parallel to each other, with the axis of studs 262 and 263 and lines drawn normal to the base surface of the ball socket defining angles larger than the angle defined by the axis of stud 261 and the radial axis 265 of the ball socket. In the socket illustrated in the figures, the axis of the stud 261 forms an angle 267 of 10° with the main axis 265 of the ball socket 250, and the axes of the studs 262 and 263 each form an angle 270 of 25° with respect to normals drawn to the base surface 269 of the ball socket 250. The stud 261 is provided at its root with a peripheral groove 272, while each of the two other studs 262 and 263 is provided with an undercut 274 outwardly directed from the main axis 265 of the ball socket 250. These undercuts provide an improved anchorage in the pelvic bone.

The ball socket 250 is provided at its lower edge with a cavity 275 at one side thereof proceeding from the base surface 269. The sickel shaped formation of this cavity, as seen in plan view, is clear from the assumed external contour of the ball socket 250 shown in dotted lines in FIG. 21. This cavity 275 is provided for the unimpeded progression of the musculous iliopsoas subsequent to the implantation, and is positioned, for the other hip joint, in the mirror image position with respect to the central plane of the ball socket 250 containing the axis of the stud 261. As may be seen in FIG. 21, the cavity 275 begins at least approximately in a plane that extends through the radial axis 265 of the socket and through stud 262, and extends over an annual range of at least approximately 120° to that side of the ball socket remote from stud 263. In the illustrated socket, cavity 275 extends over an angle 276 of about 125 degrees.

Figure 22:
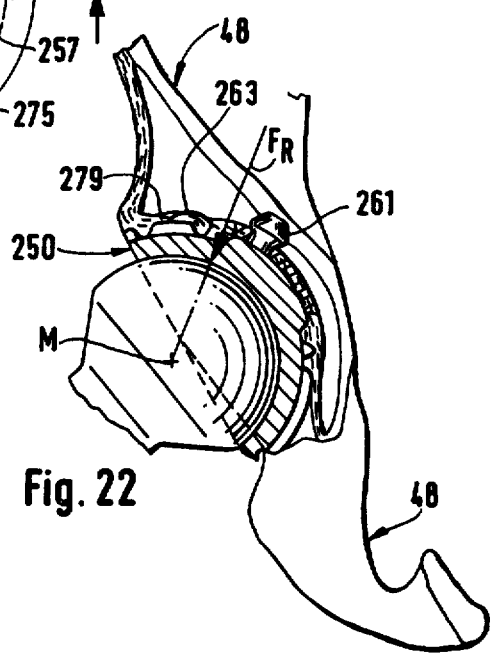
FIG. 22 is a longitudinal section through the ball socket according to FIGS. 20 and 21 with the corresponding ball.

FIG. 22 shows the ball socket 250 fitted in its assembled position in the pelvic bone 48. In order to prepare the pelvic bone for the implant, the physiological hip joint socket is first of all milled out with a spherical milling tool. In this spherical milled cavity three bores are made for the studs 261, 262 and 263 by means of a drilling template. In this operation the bores are concentrated somewhat closer together than a distance 278 shown in FIG. 20.

Thereafter the ball socket 250 is inserted in such a manner that the undercuts 274 of the studs 262 and 263 are guided over the edge of the cortical tissue 279 of the pelvic bone 48. In this operation the adjacent spongy bone is displaced towards the side. Thereafter the ball socket 250 is gradually inserted into the milled out spherical cavity until the stud 261 snaps into its bore. During this snapping in operation, the cortical tissue 279 between the studs is elastically deformed and, after springing back, locks the ball socket 250 in the inserted position according to FIG. 22.

The special position of the studs 261, 262 and 263 with reference to the resultant force $F_R$ has the result that in the studs additional thrust stresses do not arise by the elastic deformation of the bone under the influence of the resultant force $F_R$ when this force assumes its maximum value. Thus, the possible thrust stresses remain at a minimum value.

The ball socket 250 can be metallic and can be coated with enamel over its entire surface.

FIGS. 23 to 29 show a total elbow joint endoprosthesis 290. As in the case of the foregoing figures, similar parts are indicated by the same reference characters.

In this case, the shaft 73 is screwed into a humerus bone 293. The extension member 83 is provided with a downwardly pointing stop 295, shown in FIGS. 23, 24, 26 and 27, for a bearing shell 297, which does not appear in FIG. 23 and is shown inserted in an ulna 299 in FIGS. 24, 26 and 27. The bearing shell 297 is provided with an abutment surface 300 (FIG. 29) for the purpose of making contact with the stop 295, which precisely defines the extended position of the humerus 293 and the ulna 299. The side surfaces 302 and 303 (FIG. 28) of the bearing shell 297 are axially guided by corresponding opposite faces of condylar shells 305 and 306, each of which is provided with a support arm or hinge fork 105 that contains an eye for the hinge joint 102.

A hinge pin 308, which forms the first body joint member, is rotatably mounted in the bearing shell 297, which forms the second body joint member. The hinge pin 308 is made integrally with the condylar shells 305 and 306 by means of only a comparatively short connecting member 310 and 311 (FIGS. 26 and 27) of substantially semicircular cross sectional area. Each connecting member 310, 311 is situated only in that peripheral region of the hinge pin 308 which is embraced by the appertaining condylar shell 305, 306. This provides an enlarged seating surface.

Each condylar shell 305 and 306 furthermore is provided with a hole 313 for a bone screw 315 (FIG. 27) in the section of the shell which is free of the connecting piece 310, 311. After the mounting of the condylar shells upon the suitably prepared condyles 317 and 318 (FIG. 25), the screws 315 are screwed into these condyles for the purpose of temporarily anchoring the prosthesis. The connecting members 310 and 311 are comparatively small so that as much as possible of the bone substance of the condyles 317 and 318 can be left standing during the preparation of the bed of the implant for anchoring the bone screws 315. Moreover, with this construction the musculature can be protected as its osseous connections.

For the implantation of the elbow endoprosthesis, first of all the distal upper arm bone 293 is milled out in order to make it possible to provide a tapped bore for the external rounded thread 75 of the shaft 73. Following this the contact surfaces for the condylar shells are milled. Moreover, the space for the extension member 83 and its stop 295 are milled out. When this milling operations have been completed, the conical sleeve 82 is mounted upon the cone 79 and secured by the screw 87, said conical sleeve having the pivot member 320, which includes the condylar shells 305 and 306 as well as the hinge pin 308, linked to it by the hinge joint 102. Then the two bone screws 315 are driven into the condyles 317 and 318 of the upper arm bone 293. In this manner the pivoting member 320 is temporarily secured. Its final fixing to the upper arm bone 293 should again be followed by ingrowth of the bone cells into the pores of the inner condylar shell surface.

In FIGS. 24 and 27 a start of muscle 323 is shown in each case at the ulna 299.

The bearing shell 297 is provided at its rear side with anchorage projections in the form of a stud 325 and a tongue 327 arranged in spaced relation to and directed away from the stud 325. The stud 325 is provided at its root with a peripheral channel 329.

For making the implantation, first of all the proximal ulna 299 is prepared by milling out the cylindrical hollow shell of the physiological joint to the external radius of the bearing shell 297, and by milling off both sides of the elbow protruberance (olecranon) to the width of the bearing shell 297 so as to accept a drilling and milling template. By the aid of this template there are made a slot for the tongue 327 and a bore for the stud 325. The bearing shell 297 is first of all inserted with the tongue in the appertaining slot, and then is "snapped" with the stud 325 in the appertaining bore. This provides a firm seating of the shell in the ulna. The connection is completed by the later ingrowth of bone cells into the porous bearing shell surface at the contact surfaces of the bone sections.

From the upper edge of the condylar shells 305 and 306 to the lower termination of the externally rounded threads 75 of the shaft 73 there will exist no positive connection made through bone material between the prosthesis and its bone support, so that micro relative movements of the contact surfaces between the implant and the bone are decisively reduced. In correspondence with the various hip joints it is also possible for the total elbow joint endoprosthesis 290 to be made of metal, whose entire surface is enamelled. The bone screws 315 can also be fully enamelled.

For the purpose of the elbow joint implant, a hinge joint 102 has been described as an example with reference to FIGS. 23 to 29. However, in place of the illustrated hinge joint 102, it is possible to use for the elbow joint implant other types of pivot joints which have been described above in connection with the hip joint implant. Also, while a hip joint has been selected as an example of a body ball joint, and an elbow joint has been selected as an example of a body hinge joint suitable for the fitting of a prosthesis, it should be noted that the above disclosed principles are also basically applicable to all other body joints.

FIGS. 30–33 illustrate an instrument for inserting the shaft 73 for the hip joint prostheses illustrated above in a threaded hole in the thigh bone previously prepared, for example, with a self-centering conical boring tool. The instrument may also be used to precisely mill the femur for insertion of the pivot member 107 of these prostheses, and to remove the shaft 73.

Figure 30:
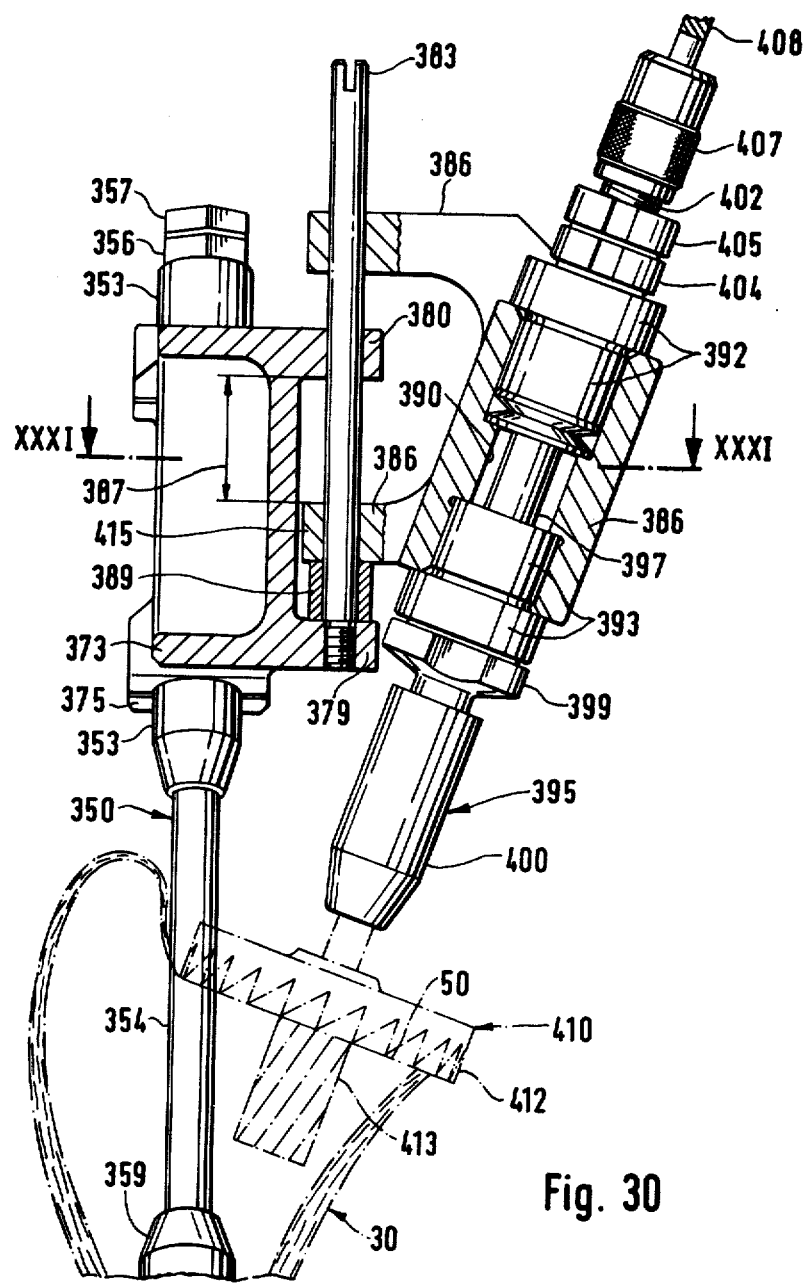
FIG. 30 is the sectional elevation along the line XXX—XXX in FIG. 31 of an instrument for the insertion and removal of a body joint endoprosthesis.
Figure 31:
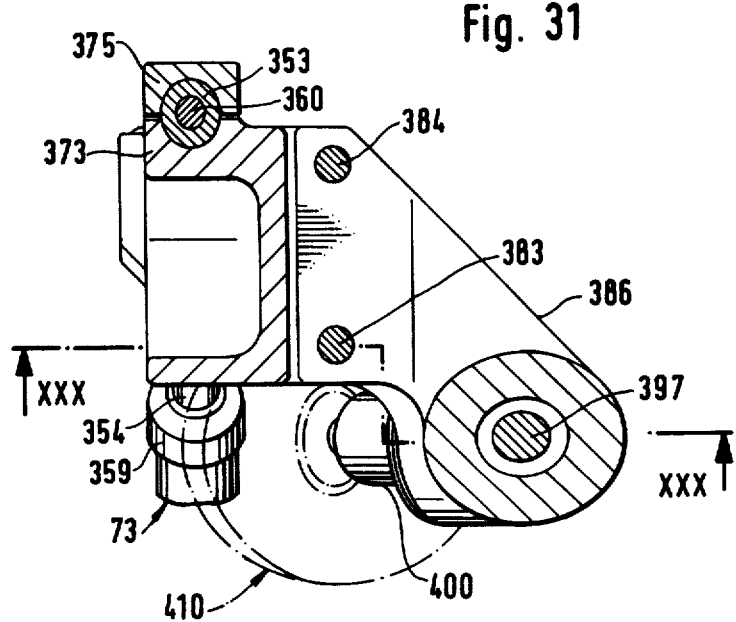
FIG. 31 is the sectional elevation along the line XXXI—XXXI in FIG. 30.

FIG. 30 shows a rotary tool 350 having two tubes 353 and 354 rigidly connected together. The tube 353 carries at its upper end a key surface 356 and a screw plug 357 threaded into the tube 353. At the lower end of the tube 354 there is secured a conical socket 359 complementary to the cone 79 at the top of shaft 73.

As shown in FIG. 32 a threaded screw 360 passes through the interior of the tubes 353 and 354, and is threaded into the tapped bore 80 in the cone 79 of the shaft 73. By means of the screw 360 and the complementary conical socket 359, the rotary tool 350 can be coupled to the shaft 73 to form a rigid unit. When the shaft is being screwed into or out of the tapped hole in the thigh bone, the longitudinal axis of this unit coincides with the axis of the tapped hole. Thus, the shaft can be screwed in or out without any bending moments, and undesired stresses on the bone are avoided.

A head 363 of the screw 360 bears against a shoulder 365 of the tube 353. The screw plug 357 is provided with a central bore 367 and its lower surface maintains a certain clearance from the upper surface of the screw head 363. Through the bore 367 of the screw plug 357, a hexagon socket key can be inserted into the hexagon socket of the head 363 for the purpose of rotating the screw 360. When the screw 360 is rotated back out of the position shown in FIG. 32, the screw 360 moves axially upwards relative to the tubes 353 and 354 until the upper surface of the head 363 bears against the lower surface of the screw plug 357 which forms a stop 370. From this instant the described relative motion ceases and upon continuing the rotation of the screw 360 the conical socket 359 is withdrawn from the cone 79. To prevent the screw plug 357 working loose, it is provided with a left hand thread 371.

With the shaft 73 screwed into the thigh bone 30, when milling operations are to be carried out upon this bone, a holder 373 is externally mounted upon the tube 353, as shown in FIGS. 30 to 33, and is clamped in the desired angular position with reference to the tube 353 by means of a clamp 375 and clamping screws 377.

In two cantilevers 379 and 380 of the holder 373 there are secured two guide bolts 383 and 384 screwed into the cantilever 379. A carrier 386 is mounted on the guide bolts and is axially displaceable along the bolts through a length of feed path 387. Between the carrier 386 and the lower cantilever 379 of the holder 373, a tubular spacing member 389 is fitted upon the guide bolt 383 to determine the magnitude of the feed path 387. Spacing members 389 of different axial length may therefore be fitted for varying the length of the feed path 387.

In an aperture 390 (FIG. 30) of the carrier 386 a milling tool 395 is mounted upon combined axial and radial bearings 392 and 393. The milling tool 395 is provided with a continuous shaft 397, which carries at its lower end a key surface 399 and a quick change clamping chuck 400, and at its upper end a threaded section 402. Upon the threaded section 402 there are mounted two counteracting fluted nuts 404 and 405 which are tightened up with respect to the key surface 399 so as to apply to the bearings 392 and 393 the correct axial stress. Upon the threaded section 402 there is also applied a union nut 407 of a flexible shaft 408 driven by a motor, not shown in the drawing.

In the quick change clamping chuck 400 there is clamped a combination milling tool 410, comprising an end miller 412 and a cylindrical milling cutter 413 projecting from the base of the end milling cutter 412.

At the beginning of the milling operation the milling tool 395 is in a starting position, in which the carrier 386 is supported with its lower projecting arms 415 (FIG. 30) bearing against the lower side of the upper cantilever 380 of the holder 373. The flexible shaft 408 is then driven so that the combination milling tool 410 rotates at the desired speed. The milling tool 395 is then fed by hand downwardly along the two guide bolts 383 and 384, whereby initially the cylindrical milling tool 413 mills out a hole inside the thigh bone 30, whereafter the end milling tool 412 comes more and more into engagement with the thigh bone 30 until, in the end position shown in FIG. 30 the seating surface 50 containing spongiose and cortical tissue is completed for the endoprosthesis. The plane of the seating surface 50 is thus precisely defined with reference to the longitudinal axis of the shaft 73, so that during the entire further course of the operation any further fitting of the remaining part of the prosthesis is unnecessary. This method shortens the operation time, protects the patient and affords a precisely defined seating for the endoprosthesis.

The angle between the axis of the rotary tool and the milling tool can be suited to all kinds of anatomical requirements by suitable design of the holder 373. As was mentioned above, this adaptation to anatomical requirements may be effected by inserting spacing members 389 of varying length between the carrier 386 and the holder 373. Thus, the depth of the milling may be reliably limited.

Figure 34:
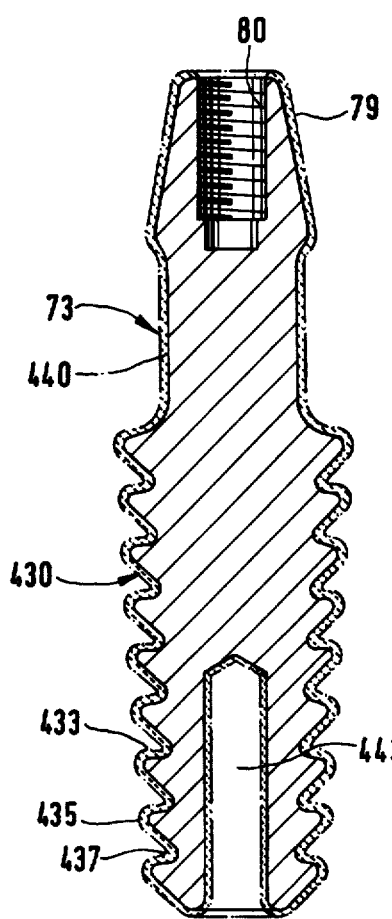
FIG. 34 is a longitudinal section through a shaft having a sawtooth thread.

FIG. 34 shows a modified form of shaft 73 with a thread 430 of sawtooth shape, which tapers conically downwards towards its distal end to suit the shape of the inner wall of the cortical tissue of the receiving bone, instead of the symmetrical external round thread shown in the previous figures. The steep flanks 433 of the sawtooth thread 430 point towards the proximal end of the shaft 73 and are directed normal to the longitudinal axis of the shaft 73. Since the flanks 433 are normal to the axis of the shaft, and to the tractive force $F_z \cdot \cos \beta$ that acts upwardly along the axis of the shaft, the sawtooth thread eliminates radial forces on the bone resulting from this tractive force, which could exert a non-physiological bursting effect on the bone.

The crests 435 of the teeth and the valleys 437 of the teeth are in each case rounded. This ensures that the bone which is situated opposite to the sawtooth thread 430 after insertion thereof is carefully treated and facilitates the application of an enamel coating 440, shown in chain and dotted lines in FIG. 34, over the entire shaft 75 with the exception of the threaded bore 80. A bore 443, which is also enamelled, is made in the bottom of the shaft 73, into which a deposit is inserted, for example an antibotic, before the fitting of the shaft 73. For promoting the ingrowth of the surrounding bone tissue into the shaft 73, the enamel coating can be externally roughened.

This sawtooth thread can also be designed to be self-cutting by locally interrupting the thread in the axial direction and providing it with cutting edges.

We claim:
1. A body joint endoprosthesis comprising:
   an anchoring part comprising a shaft adapted to be anchored in a first bone;
   a pivot member comprising a first joint member and a support element adapted to bear against a seating surface of the first bone, said pivot member being connected to said anchoring part by a joint that permits said support element to pivot in a direction substantially normal to said seating surface; and
   a second joint member adapted to be connected to a second bone, with said first joint member and said second joint member forming a body implant joint.
2. A body joint endoprosthesis according to claim 1 wherein said anchoring part comprises an extension member releasably connected to said shaft.
3. A body joint endoprosthesis according to claim 2 wherein there is a cone, having a tapped bore, at an end of said shaft and said extension member comprises a complementary conical socket mounted upon said cone and a screw, inserted into said tapped bore, that urges said socket against said cone.
4. A body joint endoprosthesis according to claim 1 wherein said pivot joint is a hinge joint.
5. A body joint endoprosthesis according to claim 1 wherein said pivot joint is a ball joint.
6. A body joint endoprosthesis according to claim 1 wherein the pivot joint is a Cardan joint.
7. A body joint endoprosthesis according to claim 1 wherein the pivot joint is a knife bearing joint.
8. A body joint endoprosthesis according to claim 1 wherein the pivot joint is an elastic joint.
9. A body joint endoprosthesis according to claim 8, wherein the pivot joint comprises at least one pre-stressed resilient member that connects said anchoring part to said pivot member and urges said support element toward said seating surface.
10. A body joint endoprosthesis according to claim 9 wherein said resilient member is a leaf spring.
11. A body joint endoprosthesis according to claim 9, wherein two resilient members are arranged for pivotal movement in a common plane and are spaced from one another in a parallelogram arrangement.
12. A body joint endoprosthesis according to claim 1 wherein a spring, located between said anchoring part and said pivot member, urges said support element toward said seating surface.
13. A body joint endoprosthesis according to claim 12 wherein said spring is located between the pivot member and a clamping screw screwed into a pivotable stud mounted on said anchoring part.
14. A hip joint endoprosthesis according to claim 1 wherein the first bone is a thigh bone, the first joint member comprises a ball, and the support element comprises a collar secured to said ball.
15. A hip joint endoprosthesis according to claim 14 wherein said pivot member pivots about a point or an axis located at least approximately in a plane containing said seating surface.
16. A hip joint endoprosthesis according to claim 14 wherein said second bone comprises a pelvic bone and said second joint member comprises a ball socket having button-like studs for anchorage in the pelvic bone.
17. A hip joint endoprosthesis according to claim 16 wherein said ball socket includes first, second and third studs arranged at the corners of a triangle so that the maximum resultant force upon the body joint passes substantially through the surface center of gravity of said triangle.

18. A hip joint endoprosthesis according to claim 17 wherein said first stud is located near the apex of said socket and said second and third studs are located at substantially one-half the height of said socket.

19. A hip joint endoprosthesis according to claim 18 wherein the axes of said first, second and third studs lie in substantially mutually parallel planes, and the axes of said second and third studs enclose greater angles than the axis of said first stud with normals to a base surface of said ball socket.

20. A hip joint endoprosthesis according to claim 19 wherein said first stud has a circumferential channel at its foot and said second and third studs each have an undercut configuration directed outwardly from the axis of said ball socket.

21. A hip joint endoprosthesis according to claim 18 wherein the edge of said ball socket includes a cavity, said cavity beginning at least approximate in a plane that extends through the axis of the socket and through said second stud, said cavity extending over an annular range of at least about 120° to the side of the ball socket remote from said third stud.

22. A hip joint endoprosthesis according to claim 16 wherein said ball socket has a plurality of concentric channels and a plurality of channels lying in planes passing through the axis of the socket.

23. An elbow joint endoprosthesis according to claim 1 wherein said first bone is an upper arm bone, the first joint member comprises a hinge pin and the support element comprises two spaced condylar shells connected to the ends of said hinge pin.

24. An elbow joint endoprosthesis according to claim 23 wherein each condylar shell includes a support arm bearing a part of the pivot joint.

25. An elbow joint endoprosthesis according to claim 23 wherein the anchoring part includes a stop for limiting pivotal movement of the second joint member.

26. An elbow joint endoprosthesis according to claim 23 wherein the second bone is an ulna, the second joint member comprises a bearing shell for the hinge pin, and the bearing shell is provided with projections for anchorage to the ulna.

27. An elbow joint endoprosthesis according to claim 26 wherein end faces of the bearing shell are axially guided by the condylar shells.

28. An elbow joint endoprosthesis comprising:
an anchoring part comprising a shaft adapted to be anchored in an upper arm bone;
a pivot member connected to said anchoring part by a pivot joint, said pivot member comprising a hinge pin and two spaced condylar shells connected to the ends of said hinge pin and adapted to bear against a seating surface of said upper arm bone, said hinge pin and said condylar shells being made in one piece; and
a second joint member adapted to be connected to a second bone, with said hinge pin and said second joint member forming an elbow implant joint.

29. An elbow joint endoprosthesis comprising:
an anchoring part comprising a shaft adapted to be anchored in an upper arm bone;
a pivot member connected to said anchoring part by a pivot joint, said pivot member comprising a hinge pin and two spaced condylar shells adapted to bear against a seating surface of said upper arm bone, said hinge pin being connected to each of said condylar shells by a short connecting piece, with the part of each shell free from the connecting piece containing a perforation for a bone screw; and
a second joint member adapted to be connected to a second bone, with said hinge pin and said second joint member forming an elbow implant joint.

30. An elbow joint endoprosthesis according to claim 29, wherein each connecting piece is located only in the peripheral region of the hinge pin surrounded by the associated condylar shell.

31. An elbow joint endoprosthesis comprising:
an anchoring part comprising a stop and a shaft adapted to be anchored in an upper arm bone;
a pivot member connected to said anchoring part by a pivot joint, said pivot member comprising a hinge pin and two spaced condylar shells adapted to bear against a seating surface of the upper arm bone; and
a cylindrical half shell adapted to be connected to an ulna and having projections for anchorage to the ulna, said shell having an end face comprising an abutment surface for making contact with said stop in the extended position of the upper arm bone and ulna, with said hinge pin and said shell forming an elbow implant joint and said stop limiting pivotal movement of said shell.

32. An elbow joint endoprosthesis comprising:
an anchoring part comprising a shaft adapted to be anchored in an upper arm bone;
a pivot member connected to said anchoring part by a pivot joint, said pivot member comprising a hinge pin and two spaced condylar shells adapted to bear against a seating surface of the upper arm bone; and
a bearing shell adapted to be connected to an ulna, with said hinge pin and said bearing shell forming an elbow implant joint, said shell having anchorage projections located in the central transverse plane of said bearing shell for anchorage to the ulna, said anchorage projections comprising a stud having a peripheral channel and a tongue directed away from the stud and spaced from the stud.

* * * * *